United States Patent [19]

Schwark et al.

[11] Patent Number: 5,756,535
[45] Date of Patent: May 26, 1998

[54] SUBSTITUTED THIOPHENYLALKENYLCARBOXYLIC ACID GUANIDINES, PROCESSES FOR THEIR PREPARATION, THEIR USE AS A MEDICAMENT OR DIAGNOSITC, AND A MEDICAMENT CONTAINING THEM

[75] Inventors: Jan-Robert Schwark, Frankfurt; Joachim Brendel, Bad Vilbel; Heinz-Werner Kleemann, Bischofsheim; Hans Jochen Lang, Hofheim; Andreas Weichert, Egelsbach; Udo Albus, Florstadt; Wolfgang Scholz, Eschborn, all of Germany

[73] Assignee: Hoechst Aktiengesellschaft, Frankfurt am Main, Germany

[21] Appl. No.: 798,259

[22] Filed: Feb. 11, 1997

[30] Foreign Application Priority Data

Feb. 15, 1996 [DE] Germany .................. 196 05 610.1

[51] Int. Cl.⁶ .................. A61K 31/38; C07D 333/32
[52] U.S. Cl. .................. 514/445; 514/438; 549/65; 549/76
[58] Field of Search .................. 549/65, 76; 514/445, 514/438

[56] References Cited

U.S. PATENT DOCUMENTS

| 2,734,904 | 2/1956 | Burtner et al. | 549/76 |
| 4,544,670 | 10/1985 | Studt et al. | 514/617 |
| 5,567,734 | 10/1996 | Schwark et al. | 514/617 |

FOREIGN PATENT DOCUMENTS

| 2172095 | 1/1996 | Australia |
| 8400875 | 3/1984 | WIPO |

OTHER PUBLICATIONS

Eur. Heart J. 9(suppl.1): 167 (1988) book of abstracts.
Circulation 79, pp. 1257–1263 (1989).

*Primary Examiner*—Deborah Lambkin
*Attorney, Agent, or Firm*—Finnnegan, Henderson, Farabow, Garrett & Dunner, L.L.P.

[57] ABSTRACT

Substituted thiophenylalkenylcarboxylic acid guanidides, processes for their preparation, their use as a medicament or diagnostic, and a medicament containing them.

There are described substituted thiophenylalkenylcarboxylic acid guanidides of the formula I

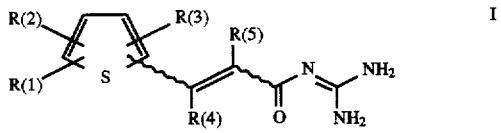

in which R(1) to R(5) have the meanings given in the claims, which are outstandingly active antiarrhythmic pharmaceuticals having a cardioprotective component and are outstandingly suitable for infarct prophylaxis and infarct treatment and also for the treatment of angina pectoris, where they also inhibit or greatly reduce the pathophysiological processes in the formation of ischemically induced damage, in particular in the initiation of ischemically induced cardiac arrhythmias, in a preventive manner.

25 Claims, No Drawings

SUBSTITUTED THIOPHENYLALKENYLCARBOXYLIC ACID GUANIDINES, PROCESSES FOR THEIR PREPARATION, THEIR USE AS A MEDICAMENT OR DIAGNOSITC, AND A MEDICAMENT CONTAINING THEM

SUMMARY OF THE INVENTION

The invention relates to substituted thiophenylalkenylcarboxylic acid guanidides of the formula I

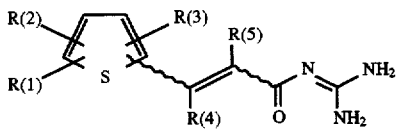

in which:

at least one of the substituents R(1), R(2) and R(3) is
—Op—(CH$_2$)$_s$—C$_q$F$_{2q+1}$R(40)CO— or R(31)SO$_k$—;
p is zero or 1;
s is zero, 1, 2, 3 or 4;
q is 1, 2, 3, 4, 5, 6, 7 or 8;
k is zero, 1 or 2;
R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is unsubstituted or substituted by 1–3 substituents selected from the group consisting of F, Cl, CF$_3$, methyl and methoxy;
R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is unsubstituted or substituted by 1–3 substituents selected from the group consisting of F, Cl, CF$_3$, methyl and methoxy;
or
R(31) is NR(41)R(42);
R(41) and R(42) independently of one another are hydrogen, alkyl having 1, 2, 3 or 4 carbon atoms, perfluoroalkyl having 1, 2, 3 or 4 carbon atoms,
or
R(41) and R(42) together are 4 or 5 methylene groups, of which one CH$_2$ group can be replaced by oxygen, S, NH, N—CH$_3$ or N-benzyl;
and the other substituents R(1), R(2) and R(3) in each case independently of one another are H, F, Cl, Br, I, CN, —O$_{na}$—C$_{ma}$H$_{2ma+1}$ or —O$_{ga}$C$_{ra}$H$_{2ra}$R(10);
na is zero or 1;
ma is zero, 1, 2, 3, 4, 5, 6, 7 or 8;
ga is zero or 1;
ra is zero, 1, 2, 3 or 4;
R(10) is cycloalkyl having 3, 4, 5, 6, 7 or 8 carbon atoms or phenyl, the phenyl being unsubstituted or substituted by 1–3 substituents selected from the group consisting of F, Cl, CF$_3$, methyl and methoxy;
R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl,
which is unsubstituted or substituted by 1–3 substituents selected from the group consisting of F, Cl, CF$_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;
and their pharmaceutically tolerable salts.

Preferred compounds of the formula I are those in which:
at least one of the substituents R(1), R(2) and R(3) is
—OP(CH$_2$)$_s$—C$_q$F$_{2q+1}$R(40)CO— or R(31) SO$_k$—;
p is zero or 1;
s is zero, 1 or 2;
q is 1, 2, 3 or 4;
k is zero or 2;
R(40) is alkyl having 1, 2, 3 or 4 carbon atoms, perfluoroalkyl having 1, 2, 3 or 4 carbon atoms or phenyl,
which is unsubstituted or substituted by 1–3 substituents selected from the group consisting of F, Cl, CF$_3$, methyl and methoxy;
R(31) is alkyl having 1, 2, 3 or 4 carbon atoms, perfluoroalkyl having 1, 2, 3 or 4 carbon atoms or phenyl,
which is unsubstituted or substituted by 1–3 substituents selected from the group consisting of F, Cl, CF$_3$, methyl and methoxy;
or
R(31) is NR(41)R(42);
R(41) and R(42) independently of one another are hydrogen, CH$_3$ or CF$_3$;
or
R(41) and R(42) together are 4 or 5 methylene groups, of which one CH$_2$ group can be replaced by oxygen, S, NH, N—CH$_3$ or N-benzyl;
and the other substituents R(1), R(2) and R(3) in each case independently of one another are H, F, Cl, Br, I, CN, —O$_{na}$—C$_{ma}$H$_{2ma+1}$ or —O$_{ga}$C$_{ra}$H$_{2ra}$R(10);
na is zero or 1;
ma is zero, 1, 2, 3 or 4;
ga is zero or 1;
ra is zero, 1 or 2;
R(10) is cycloalkyl having 3, 4, 5, 6, 7 or 8 carbon atoms or phenyl, which is unsubstituted or substituted by 1–3 substituents selected from the group consisting of F, Cl, CF$_3$, methyl and methoxy;
R(4) and R(5) independently of one another are hydrogen, F, Cl, alkyl having 1, 2, 3 or 4 carbon atoms, perfluoroalkyl having 1, 2, 3 or 4 carbon atoms, cycloalkyl having 5, 6, 7 or 8 carbon atoms or phenyl,
which is unsubstituted or substituted by 1–3 substituents selected from the group consisting of F, Cl, CF$_3$, methyl, methoxy and NR(14)R(15);
R(14) and R(15) independently of one another are hydrogen, CH$_3$, CF$_3$;
and their pharmaceutically tolerable salts.

Particularly preferred compounds of the formula (I) are those in which:
at least one of the substituents R(1), R(2) and R(3) is
—Op—(CH$_2$)$_s$—C$_q$F$_{2q+1}$ or R(31) SO$_k$—;
p is zero or 1;
s is zero;
q is 1;
k is zero or 2;
R(31) is CH$_3$, CF$_3$ or phenyl,
which is unsubstituted or substituted by 1–3 substituents selected from the group consisting of F, Cl, CF$_3$, methyl and methoxy;
or
R(31) is NR(41)R(42);
R(41) and R(42) independently of one another are hydrogen, CH$_3$ or CF$_3$;

or

R(41) and R(42) together are 4 or 5 methylene groups, of which one CH$_2$ group can be replaced by oxygen, S, NH, N—CH$_3$ or N-benzyl;

and the other substituents R(1), R(2) and R(3) in each case independently of one another are H, F, Cl, CN, —O$_{na}$—C$_{ma}$H$_{2ma+1}$ or —O$_{ga}$C$_{ra}$H$_{2ra}$R(10);

na is zero or 1;
ma is zero, 1, 2, 3 or 4;
ga is zero or 1;
ra is zero or 1;

R(10) is phenyl, which is unsubstituted or substituted by 1–3 substituents selected from the group consisting of F, Cl, CF$_3$, methyl and methoxy;

R(4) and R(5) independently of one another are hydrogen, F, Cl, CH$_3$, CF$_3$;

and their pharmaceutically tolerable salts.

Very particularly preferred compounds of the formula I are those in which:

at least one of the substituents R(1), R(2) and R(3) is R(31)SO$_k$—;

k is zero or 2;

R(31) is CH$_3$, CF$_3$ or phenyl,
which is unsubstituted or substituted by 1–3 substituents selected from the group consisting of F, Cl, CF$_3$, methyl and methoxy;

or

R(31) is NR(41)R(42);

R(41) and R(42) independently of one another are hydrogen, CH$_3$ or CF$_3$;

or

R(41) and R(42) together are 4 or 5 methylene groups, of which one CH$_2$ group can be replaced by oxygen, S, NH, N—CH$_3$ or N-benzyl;

and the other substituents R(1), R(2) and R(3) in each case independently of one another are H, F, Cl, CN, —O$_{na}$—C$_{ma}$H$_{2ma+1}$ or —O$_{ga}$C$_{ra}$H$_{2ra}$R(10);

na is zero or 1;
ma is zero, 1, 2, 3 or 4;
ga is zero or 1;
ra is zero or 1;

R(10) is phenyl, which is unsubstituted or substituted by 1–3 substituents selected from the group consisting of F, Cl, CF$_3$, methyl and methoxy;

R(4) and R(5) independently of one another are hydrogen, F, Cl, CH$_3$, CF$_3$;

and their pharmaceutically tolerable salts.

Specially particularly preferred compounds are:

E-3-[2-(4-methylsulfonylthiophenyl)]propenoic acid guanidide,

E-3-[2-(5-methylthiophenyl)]-2-methylpropenoic acid guanidide,

E-3-[2-(5-methylsulfonylthiophenyl)]-2-methylpropenoic acid guanidide,

E-3-[2-(3-chloro-4-isopropylsulfonyl-5-methylthiothiophenyl)]-2-methyl propenoic acid guanidide and E-3-[2-(3-chloro-4-isopropylsulfonyl-5-methylsulfonylthiophenyl)]-2-methyl propenoic acid guanidide and their pharmaceutically tolerable salts.

If the compounds of the formula I contain one or more centers of asymmetry, these can have either the S or the R configuration. The compounds can be present as optical isomers, as diastereomers, as racemates or as mixtures thereof.

The double bond geometry of the compounds of the formula I can be either E or Z. The compounds can be present in the mixture as double bond isomers.

The designated alkyl radicals and perfluoroalkyl radicals can be either straight-chain or branched.

The invention furthermore relates to a process for the preparation of the compound 1, which comprises reacting a compound of the formula II

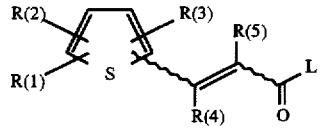

in which R(1) to R(5) have the meaning indicated and L is a leaving group which can be easily nucleophilically substituted, with guanidine.

DETAILED DESCRIPTION OF THE INVENTION

The disclosure of German Application No. 19605610.1, filed Feb. 15, 1996 is hereby incorporated by reference.

The activated acid derivatives of the formula 11 in which L is an alkoxy group, preferably a methoxy group or a phenoxy group, phenylthio, methylthio or 2-pyridylthio group, a nitrogen heterocycle, preferably 1-imidazolyl, are advantageously obtained in a manner known per se from the carbonyl chlorides (formula 11, L=Cl) on which they are based, which for their part can in turn be prepared in a manner known per se from the carboxylic acids (formula 11, L=OH) on which they are based, for example using thionyl chloride. Beside the carbonyl chlorides of the formula 11 (L=Cl), other activated acid derivatives of the formula 11 can also be prepared directly in a manner known per se from the benzoic acid derivatives (formula 11, L=OH) on which they are based, such as, for example, the methyl esters of the formula 11 where L=OCH$_3$ by treating with gaseous HCl in methanol, the imidazolides of the formula 11 by treating with carbonyldiimidazole (L=1-imidazolyl, Staab, Angew. Chem. Int. Ed. Engl. 1, 351–367 (1962)], the mixed anhydrides 11 with Cl—COOC$_2$H$_5$ or tosyl chloride in the presence of triethylamine in an inert solvent, and also the activation of benzoic acids with dicyclohexylcarbodiimide (DCC) or with O-[(cyano(ethoxycarbonyl)methylene) amino]-1,1,3,3-tetramethyluronium tetrafluoroborates ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are given stating source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Here, in the reaction of the methyl benzoates (II, L=OMe) with guanidine, methanol, isopropanol or THF from 20° C. up to the boiling temperature of these solvents have proven suitable. Most reactions of compounds 11 with salt-free guanidine were advantageously carried out in aprotic inert solvents such as THF, dimethoxyethane or dioxane. However, water can also be used in the reaction of II with guanidine, using a base such as, for example, NaOH as a solvent.

If L=Cl, the reaction is advantageously carried out with addition of an acid scavenger, e.g. in the form of excess guanidine for removing the hydrohalic acid.

Some of the underlying propenoic acid derivatives of the formula II are known and described in the literature. The unknown compounds of the formula II can be prepared by methods known from the literature. The alkenylcarboxylic acids obtained are reacted by one of the process variants described above to give compounds I according to the invention.

The introduction of some substituents is carried out by methods known from the literature of palladium-mediated cross-coupling of aryl halides or aryl triflates with, for example, organostannanes, organoboronic acids or organoboranes or organocopper or -zinc compounds.

In general, carboxylic acid guanidides I are weak bases and can bind acid with formation of salts. Possible acid addition salts are salts of all pharmacologically tolerable acids, for example halides, in particular hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

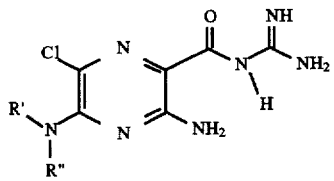

Amiloride: R', R"=H
Dimethylamiloride: R', R"=CH$_3$
Ethylisopropylamiloride: R'=C$_2$H$_5$, R"=CH(CH$_3$)$_2$ Moreover, investigations have been disclosed which point to antiarrhythmic properties of amiloride (Circulation 79, 1257–63 (1989)). An obstacle to wide application as an antiarrhythmic is, however, that this effect is only weakly pronounced and occurs accompanied by a hypotensive and saluretic action and these side effects are undesirable in the treatment of cardiac arrhythmias.

Indications of antiarrhythmic properties of amiloride were also obtained in experiments on isolated animal hearts (Eur. Heart J. 9 (suppl. 1): 167 (1988) (book of abstracts)). Thus, for example, it was found in rat hearts that it was possible to completely suppress an artificially induced ventricular fibrillation by means of amiloride. The above mentioned amiloride derivative ethylisopropylamiloride was even more potent than amiloride in this model.

WO 84/00875 discloses cinnamic acid guanidides (R$_a$ and R$_c$, or R$_b$ and R$_d$=double bond; R(1)=substituted phenyl); however, thiophene compounds are neither described nor suggested therein.

U.S. Pat. No. 2,734,904 discloses cinnamic acid guanidides (R=substituted phenyl, alkyl or alkenylene), but no thiophene compounds of the type claimed are described or suggested. Thiophenealkenylcarboxylic acid guanidides are indeed disclosed therein which, however, do not carry the essential substituents —Op—(CH$_2$)$_x$—C$_q$F$_{2q+1}$; R(40)CO— or R(31) SO$_k$—.

DE-A-44 21 536.3 (HOE 94/F 168) describes cinnamic acid guanidides; however, it likewise does not describe any thiophene compounds.

The known and also the proposed compounds do not meet, however, all the desired demands, thus their water solubility leaves something to be desired.

Additionally, they still do not act selectively to the desired extent. It was therefore desirable to make available compounds having improved water solubility and selectivity.

This has been achieved by means of the compounds according to the invention, which do not have any undesirable and disadvantageous salidiuretic properties, but have very good antiarrhythmic properties, such as are important, for example, for the treatment of illnesses which are caused by oxygen deficiency. On account of their pharmacological properties, the compounds are outstandingly suitable as antiarrhythmic pharmaceuticals having a cardioprotective component for infarct prophylaxis and infarct treatment and also for the treatment of angina pectoris, where they also inhibit or greatly reduce the pathophysiological processes in the formation of ischemically induced damage, in particular in the initiation of ischemically induced cardiac arrhythmias, in a preventive manner. Because of their protective actions against pathological hypoxic and ischemic situations, the compounds of the formula I according to the invention can be used, on account of inhibition of the cellular Na$^+$/H$^+$ exchange mechanism, as pharmaceuticals for the treatment of all acute or chronic damage caused by ischemia or illnesses primarily or secondarily induced thereby. This relates to their use as pharmaceuticals for surgical interventions, e.g. in organ transplantation, where the compounds can be used both for the protection of the organs in the donor before and during removal, for the protection of removed organs, for example during treatment with or storage thereof in physiological bath fluids, and during transfer to the recipient body. The compounds are likewise useful pharmaceuticals having a protective action when carrying out angioplastic surgical interventions, for example on the heart, and on peripheral vessels. Corresponding to their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are likewise suitable for the treatment of forms of shock, such as, for example, of allergic, cardiogenic, hypovolemic and bacterial shock.

Moreover, the compounds of the formula I according to the invention are distinguished by potent inhibitory action on the proliferation of cells, for example fibroblast cell proliferation and the proliferation of the vascular smooth muscle cells. The compounds of the formula I are therefore suitable as useful therapeutics for illnesses in which cell proliferation is a primary or secondary cause, and can therefore be used as antietherosclerotics, agents against diabetic late complications, carcinogenic disorders, fibrotic disorders such as pulmonary fibrosis, fibrosis of the liver or fibrosis of the kidneys, organ hypertrophies and hyperplasias in particular in prostate hyperplasia or prostate hypertrophy.

The compounds according to the invention are effective inhibitors of the cellular sodium-proton antiporter (Na$^+$/H$^+$ exchanger), which is raised in numerous disorders (essential hypertension, atherosclerosis, diabetes, etc.) even in those cells which are easily accessible to measurements, such as, for example, in erythrocytes, platelets or leukocytes. The compounds according to the invention are therefore suitable as outstanding and simple scientific tools, for example in their use as diagnostics for the determination and differentiation of certain forms of hypertension, but also of atherosclerosis, of diabetes, proliferative disorders, etc.

Moreover, the compounds of the formula I are suitable for preventive therapy for preventing the genesis of high blood pressure, for example of essential hypertension.

Pharmaceuticals which contain a compound I can be administered orally, parenterally, intravenously, rectally or by inhalation, the preferred administration being dependent on the particular form of the disorder. The compounds I can be used on their own or together with pharmaceutical auxiliaries, and in fact both in veterinary and in human medicine.

The auxiliaries which are suitable for the desired pharmaceutical formulation are familiar to the person skilled in the art on the basis of his expert knowledge. Beside solvents, gelling agents, suppository bases, tabletting auxiliaries, and other active compound excipients, for example, antioxidants, dispersants, emulsifiers, antifoams, flavor corrigens, preservatives, solubilizers or colorants can be used.

For a form for oral administration, the active compounds are mixed with the additives suitable for this purpose, such as excipients, stabilizers or inert diluents, and brought by means of the customary methods into suitable administration forms, such as tablets, coated tablets, hard gelatin capsules, or aqueous, alcoholic or oily solutions. Inert excipients which can be used are, for example, gum arabic, magnesia, magnesium carbonate, potassium phosphate, lactose, glucose or starch, in particular corn starch. In this case, preparation can be carried out either as dry or as moist granules. Suitable oily excipients or solvents are, for example, vegetable or animal oils, such as sunflower oil or fish liver oil.

For subcutaneous or intravenous administration, the active compounds, if desired with the substances customary for this purpose such as solubilizers, emulsifiers or other auxiliaries, are brought into solution, suspension or emulsion. Possible solvents are, for example: water, physiological saline solution or alcohols, e.g. ethanol, propanol, glycerol, in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain still further pharmaceutical auxiliaries such as surfactants, emulsifiers and stabilizers as well as a propellant. Such a preparation customarily contains the active compound in a concentration of approximately 0.1 to 10, in particular of approximately 0.3 to 3, % by weight.

The dosage of the active compound of the formula I to be administered and the frequency of administration depend on the potency and duration of action of the compounds used; additionally also on the nature and severity of the illness to be treated and on the sex, age, weight and individual responsiveness of the mammal to be treated.

On average, the daily dose of a compound of the formula I in the case of a patient of weight approximately 75 kg is at least 0.001 mg/kg, preferably 0.01 mg/kg, to at most 10 mg/kg, preferably 1 mg/kg, of body weight. In acute episodes of the illness, for example immediately after suffering a cardiac infarct, even higher and especially more frequent dosages may also be necessary, e.g. up to 4 individual doses per day. In particular in the case of i.v. administration, for example in the case of an infarct patient in the intensive care unit, up to 200 mg per day may be necessary.

List of abbreviations:

| | |
|---|---|
| MeOH | Methanol |
| DMF | N,N-Dimethylformamide |
| EI | Electron impact |
| DCI | Desorption-chemical ionization |
| RT | Room temperature |
| EA | Ethyl acetate (EtOAc) |
| m.p. | Melting point |
| HEP | n-Heptane |
| DME | Dimethyloxyethane |
| ES | Electron spray |
| FAB | Fast atom bombardment |
| CH$_2$Cl$_2$ | Dichloromethane |
| THF | Tetrahydrofuran |
| eq. | Equivalent |

EXPERIMENTAL SECTION

General instructions for the preparation of alkenylcarboxylic acid guanidides (I)

Variant A: from alkenylcarboxylic acids (II, L=OH)

1.0 eq. of the carboxylic acid derivative of the formula II is dissolved or suspended in anhydrous THF (5 ml/mmol) and then treated with 1.1 eq. of carbonyldiimidazole. After stirring for 2 hours at RT, 5.0 eq. of guanidine are introduced into the reaction solution. After stirring overnight, the THF is distilled off under reduced pressure (in a rotary evaporator), the residue is treated with water, the mixture is adjusted to pH 6 to 7 using 2 N HCl and the corresponding guanidide (formula I) is filtered off. The carboxylic acid guanidides thus obtained can be converted into the corresponding salts by treating with aqueous, methanolic or ethereal hydrochloric acid or other pharmacologically tolerable acids.

Variant B: from alkylalkenyl carboxylates (II, L=O-alkyl)

1.0 eq. of the alkyl carboxylates of the formula II and 5.0 eq. of guanidine (free base) are dissolved in isopropanol or suspended in THF and heated under reflux (typical reaction time 2 to 5 h) until conversion is complete (thin-layer checking). The solvent is distilled off under reduced pressure (rotary evaporator), the residue is taken up in EA and the solution is washed 3 times with NaHCO$_3$ solution. It is dried over Na$_2$SO$_4$, the solvent is distilled off in vacuo and the residue is chromatographed on silica gel using a suitable eluent (e.g. EA/MeOH 5:1). (Salt formation compare variant A)

Example 1

E-3-[2-(4-Methylsulfonylthiophenyl)]propenoic acid guanidide

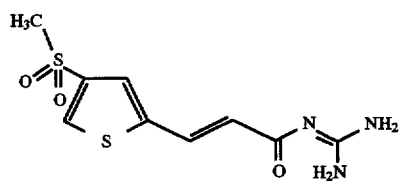

1 a) Methyl E-3-[2-(4-methylsulfonylthiophenyl)]propenoate 1 eq. of methyl 3-[2-(4-bromothiophenyl)]propenoate, 2 eq. of sodium methyl sulfinate and 2 eq. of CuI were heated under reflux in toluene/DMF (213; 3 ml/mmol of ester). Standard work-up and chromatography on silica gel (eluent: cyclohexane/EA) yielded methyl E-3-[2-(4-methylsulfonylthiophenyl)]propenoate.

m.p.: amorphous MS: 247 (M+1)$^+$ 1 b) The carboxylic acid was liberated from ester 1 a) under standard conditions (MeOH/NaOH).

m.p.: 203° C. MS: 233 (M+1)$^+$ 1 c) 1 b was converted into the guanidide hydrochloride according to general procedure A.

m.p.: 200° C. MS: 274 (M+1)$^+$

Example 2

E-3-[2-(5-Methylthiothiophenyl)]-2-methylpropenoic acid guanidide hydrochloride

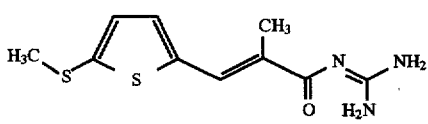

2 a) 1 eq. of triethyl 2-phosphonopropionate was deprotonated at 0° C. using 1 eq. of n-butyllithium in hexane and then treated with 1 eq. of 5-methylthiobenzaldehyde at RT. After the aldehyde had reacted to completion, the mixture was worked up with water and extracted three times by shaking with toluene. After drying the combined organic phases over magnesium sulfate, the solvent was removed in vacuo and the residual crude product was separated by chromatography on silica gel using EA/HEP mixtures as the eluent. Ethyl E-3-[2-(5-methylthiothiophenyl)]-2-methylpropenate was isolated.

Colorless oil MS: 243 (M+1)$^+$ 2 b) The ester from 2 a) was first converted into the guanidide according to variant B and then converted into the hydrochloride.

m.p.: 172° C. MS: 256 (M+1)$^+$

Example 3

E-3-[2-(5-Methylsulfonylthiophenyl)]-2-methyl propenoic acid guanidide hydrochloride

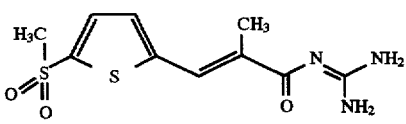

The ester from 2 a) was oxidized according to a standard reaction using 2.2 eq of m-chloroperbenzoic acid in methylene chloride to give ethyl E-3-[2-(5-methylsulfonylthiophenyl)]-2-methylpropenoate.

Colorless oil MS: 275 (M+1)$^+$ 3 b) The ester from 3 a) was first converted into the free acid using sodium hydroxide in methanol and then into the guanidide hydrochloride according to variant A. Acid.

Amorphous solid MS: 247 (M+1)$^+$

Guanidide hydrochloride:

mp:>210° C. MS: 288 (M+1)$^+$

Example 4

E-3-[2-(3-Chloro-4-isopropylsulfonyl-5-methylthiothiophenyl)]-2-methylpropenoic acid guanidide hydrochloride

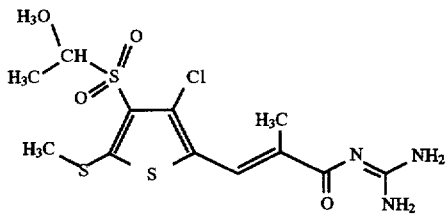

4 a) In analogy to 2 a), the commercially available 3-chloro-4-isopropyl-sulfonyl-5-methylthiothiophenyl-2-carbaldehyde was converted into the corresponding propenoic acid ester.

Colorless oil MS: 384 (M+1)$^+$ 4 b) The ester from 4 a) was converted into the guanidide according to variant B and isolated as the hydrochloride.

m.p.: 227°–235° C. MS: 396 (M+1)$^+$

Example 5

E-3-[2-(3-Chloro-4-isopropylsulfonyl-5-methylsulfonyl-thiophenyl)]-2-methylpropenoic acid guanidide hydrochloride

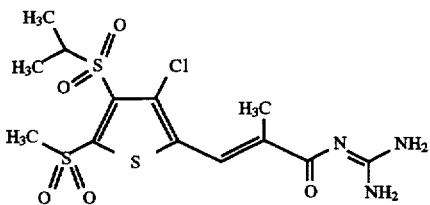

5 a) The ester from 4 a) was converted into ethyl E-3-[2-(3-chloro-4-isopropylsulfonyl-5-methylsulfonylthiophenyl)]-2-methylpropenoate with 2.2 eq of m-chloroperbenzoic acid in methylene chloride using a standard reaction.

MS: 416 (M+1)$^+$ 5 b) The ester from 5 a) was converted into the guanidide according to variant B and isolated as the hydrochloride.

MS: 428 (M+1)$^+$

What is claimed is:

1. A substituted thiophenylalkenylcarboxylic acid guanidide of the formula I

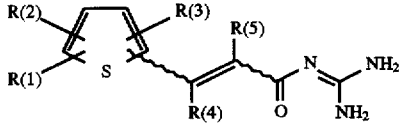

in which:

at least one of the substituents R(1), R(2) and R(3) is
—O$_p$—(CH$_2$)$_s$—C$_q$F$_{2q+1}$R(40)CO— or R(31) SO$_k$—;

p is zero or 1;

s is zero, 1, 2, 3 or 4;

q is 1, 2, 3, 4, 5, 6, 7 or 8;

k is zero, 1 or 2;

R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
   which is unsubstituted or substituted by 1-3 substituents selected from the group consisting of F, Cl, $CF_3$, methyl and methoxy;
R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
   which is unsubstituted or substituted by 1-3 substituents selected from the group consisting of F, Cl, $CF_3$, methyl and methoxy;
or
R(31) is NR(41)R(42);
   R(41) and R(42) independently of one another are hydrogen, alkyl having 1, 2, 3 or 4 carbon atoms, perfluoroalkyl having 1, 2, 3 or 4 carbon atoms,
or
   R(41) and R(42) together are 4 or 5 methylene groups, of which one $CH_2$ group can be replaced by oxygen, S, NH, N—$CH_3$ or N-benzyl;
and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}R(10)$;
na is zero or 1;
ma is zero, 1, 2, 3, 4, 5, 6, 7 or 8;
ga is zero or 1;
ra is zero, 1, 2, 3 or 4;
R(10) is cycloalkyl having 3, 4, 5, 6, 7 or 8 carbon atoms or phenyl, the phenyl being unsubstituted or substituted by 1-3 substituents selected from the group consisting of F, Cl, $CF_3$, methyl and methoxy;
R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl,
   which is unsubstituted or substituted by 1-3 substituents selected from the group consisting of F, Cl, $CF_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;
and their pharmaceutically tolerable salts.

2. A compound according to claim 1, wherein:
at least one of the substituents R(1), R(2) and R(3) is —$O_p$—$(CH_2)_s$—$C_qF_{2q+1}$R(40)CO— or R(31) $SO_k$—;
p is zero or 1;
s is zero, 1 or 2;
q is 1, 2, 3 or 4;
k is zero or 2;
R(40) is alkyl having 1, 2, 3 or 4 carbon atoms, perfluoroalkyl having 1, 2, 3 or 4 carbon atoms or phenyl,
   which is unsubstituted or substituted by 1-3 substituents selected from the group consisting of F, Cl, $CF_3$, methyl and methoxy;
R(31) is alkyl having 1, 2, 3 or 4 carbon atoms, perfluoroalkyl having 1, 2, 3 or 4 carbon atoms or phenyl,
   which is unsubstituted or substituted by 1-3 substituents selected from the group consisting of F, Cl, $CF_3$, methyl and methoxy;
or
R(31) is NR(41)R(42);
   R(41) and R(42) independently of one another are hydrogen, $CH_3$ or $CF_3$;
or
   R(41) and R(42) together are 4 or 5 methylene groups, of which one $CH_2$ group can be replaced by oxygen, S, NH, N—$CH_3$ or N-benzyl;
and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}R(10)$;
na is zero or 1;
ma is zero, 1, 2, 3 or 4;
ga is zero or 1;
ra is zero, 1 or 2;
R(10) is cycloalkyl having 3, 4, 5, 6, 7 or 8 carbon atoms or phenyl,
   which is unsubstituted or substituted by 1-3 substituents selected from the group consisting of F, Cl, $CF_3$, methyl and methoxy;
R(4) and R(5) independently of one another are hydrogen, F, Cl, alkyl having 1, 2, 3 or 4 carbon atoms, perfluoroalkyl having 1, 2, 3 or 4 carbon atoms, cycloalkyl having 5, 6, 7 or 8 carbon atoms or phenyl,
   which is unsubstituted or substituted by 1-3 substituents selected from the group consisting of F, Cl, $CF_3$, methyl, methoxy and NR(14)R(15);
R(14) and R(15) independently of one another are hydrogen, $CH_3$, $CF_3$;
and their pharmaceutically tolerable salts.

3. A compound according to either claim 1 or claim 2, wherein:
at least one of the substituents R(1), R(2) and R(3) is —$O_p$—$(CH_2)_s$—$C_qF_{2q+1}$ or R(31) $SO_k$—;
p is zero or 1;
s is zero;
q is 1;
k is zero or 2;
R(31) is $CH_3$, $CF_3$ or phenyl,
   which is unsubstituted or substituted by 1-3 substituents selected from the group consisting of F, Cl, $CF_3$, methyl and methoxy;
or
R(31) is NR(41)R(42);
   R(41) and R(42) independently of one another are hydrogen, $CH_3$ or $CF_3$;
or
   R(41) and R(42) together are 4 or 5 methylene groups, of which one $CH_2$ group can be replaced by oxygen, S, NH, N—$CH_3$ or N-benzyl;
and the other substituents R(1), R(2) and R(3) in each case independently of one another are H, F, Cl, CN, —$O_{na}$—$C_{ma}H_{2ma+1}$ or —$O_{ga}C_{ra}H_{2ra}R(10)$;
na is zero or 1;
ma is zero, 1, 2, 3 or 4;
ga is zero or 1;
ra is zero or 1;
R(10) is phenyl,
   which is unsubstituted or substituted by 1-3 substituents selected from the group consisting of F, Cl, $CF_3$, methyl and methoxy;
R(4) and R(5) independently of one another are hydrogen, F, Cl, $CH_3$, $CF_3$;
and their pharmaceutically tolerable salts.

4. A compound according to claim 1 in which:
at least one of the substituents R(1), R(2) and R(3) is R(31)$SO_k$—;
k is zero or 2;
R(31) is $CH_3$, $CF_3$ or phenyl,
   which is unsubstituted or substituted by 1-3 substituents selected from the group consisting of F, Cl, $CF_3$, methyl and methoxy;

or
R(31) is NR(41)R(42);
R(41) and R(42) independently of one another are hydrogen, CH₃ or CF₃;
or
R(41) and R(42) together are 4 or 5 methylene groups, of which one CH₂ group can be replaced by oxygen, S, NH, N—CH₃ or N-benzyl;
and the other substituents R(1), R(2) and R(3) in each case independently of one another are H, F, Cl, CN, $-O_{na}-C_{ma}H_{2ma+1}$ or $-O_{ga}C_{ra}H_{2ra}R(10)$;
na is zero or 1;
ma is zero, 1, 2, 3 or 4;
ga is zero or 1;
ra is zero or 1;
R(10) is phenyl,
which is unsubstituted or substituted by 1–3 substituents selected from the group consisting of F, Cl, CF₃, methyl and methoxy;
R(4) and R(5) independently of one another are hydrogen, F, Cl, CH₃, CF₃;
and their pharmaceutically tolerable salts.

5. A compound according to claim 1 wherein the compound is E-3-[2-(4-methylsulfonylthiophenyl)]propenoic acid guanidide.

6. A compound according to claim 1 wherein the compound is E-3-[2-(5-methylthiophenyl)]-2-methylpropenoic acid guanidide.

7. A compound according to claim 1 wherein the compound is E-3-[2-(5-methylsulfonylthiophenyl)]-2-methylpropenoic acid guanidide.

8. A compound according to claim 1 wherein the compound is E-3-[2-(3-chloro-4-isopropylsulfonyl-5-methylthiothiophenyl)]-2-methyl propenoic acid guanidide.

9. A compound according to claim 1 wherein the compound is E-3-[2-(3-chloro-4-isopropylsulfonyl-5-methylsulfonylthiophenyl)]-2-methyl propenoic acid guanidide.

10. A process for the preparation of the compound according to claim 1, which comprises,
reacting a compound of the formula:

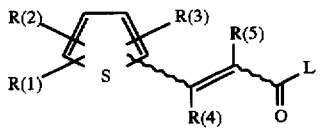

in which R(1) to R(5) have the meaning indicated and L is a leaving group which can be easily hucleophilically substituted, with guanidine.

11. A pharmaceutical composition comprising a compound according to claim 1 or a salt thereof and a pharmaceutically acceptable carrier for the production of a medicament for the treatment of arrhythmias.

12. A method for treating arrhythmias, which comprises mixing an efficacious amount of the compound I according to claim 1 with the customary additives and administering it in a suitable administration form.

13. A pharmaceutical comprising an efficacious amount of a compound according to claim 1.

14. A method for treating or preventing illnesses caused by ischemic conditions, said method comprising administering to a host in need of said treatment or prevention an effective amount of a compound of formula I or a salt thereof according to claim 1.

15. A method for treating or preventing cardiac infarct, said method comprising administering to a host in need of said treatment or prevention an effective amount of a compound of formula I or a salt thereof according to claim 1.

16. A method for treating or preventing angina pectoris, said method comprising administering to a host in need of said treatment or prevention an effective amount of a compound of formula I or a salt thereof according to claim 1.

17. A method for treating or preventing ischemic conditions of the heart, said method comprising administering to a host in need of said treatment or prevention an effective amount of a compound of formula I or a salt thereof according to claim 1.

18. A method of treating or preventing ischemic conditions of the peripheral nervous system, the central nervous system and stroke, said method comprising administering to a host in need of said treatment or prevention an effective amount of ;3 compound of formula I or a salt thereof according to claim 1.

19. A method for treating or preventing ischemic conditions of the peripheral organs and members, said method comprising administering to a host in need of said treatment or prevention an effective amount of a compound of formula I or a salt thereof according to claim 1.

20. A method for treating states of shock, said method comprising administering to a host in need of said treatment an effective amount of a compound of formula I or a salt thereof according to claim 1.

21. A pharmaceutical composition for use in surgical operations and organ transplants, which comprises an effective amount of a compound of formula I or a salt thereof according to claim I and a pharmaceutically acceptable carrier.

22. A pharmaceutical composition for use in preserving and storing transplants for surgical procedures, which comprises an effective amount of a compound of formula I or a salt thereof according to claim 1 and a pharmaceutically acceptable carrier.

23. A method for treating illnesses in which cell proliferation is a primary or secondary cause, said method comprising administering to a host in need of said treatment an effective amount of a compound of formula I or a salt thereof according to claim 1.

24. The method according to claim 23 wherein the disease in which cell proliferation is a primary or secondary cause is atherosclerosis, a late complication of diabetes, a carcinogenic disorder, a fibrotic disorder or prostate hyperplasia.

25. The method according to claim 24 wherein the fibrotic disease is pulmonary fibrosis, hepatic fibrosis, or renal fibrosis.

* * * * *

UNITED STATES PATENT AND TRADEMARK OFFICE
CERTIFICATE OF CORRECTION

PATENT NO. : 5,756,535
DATED : May 26, 1998
INVENTOR(S) : Jan-Robert Schwark, et. al.

It is certified that error appears in the above-identified patent and that said Letters Patent is hereby corrected as shown below:

Title page, item [54] and col. 1, line 5, the title should read -- DIAGNOSTIC instead of DIAGNOSITC--

Claim 1, col. 10, line 61, "$-O_p-(CH_2)_s-C_qF_2q+1R(40)CO-$" should read -- $-O_p-(CH_2)_s-C_qF_{2q+1}R(40)CO-$ --.

Claim 1, col. 11, line 27, "iszero" should read --is zero--.

Claim 2, col. 11, line 47, "$-O_p-(CH_2)_s-C_qF_{2q+1}R(40)CO-$" should read -- $-O_p-(CH_2)_s-C_qF_{2q+1}R(40)CO-$ --.

Claim 2, col. 11, line 48, "or1" should read --or 1--.

Claim 10, col. 13, line 49, "hucleophilically" should read --nucleophilically--.

Claim 14, col. 14, line 1, "fortreating" should read --for treating--.

Claim 18, col. 14, line 25, ";3" should read --a--.

Claim 21, col. 14, line 39, "claim I" should read --claim 1--.

Claim 24, col. 14, line 52, after "claim 23", insert --,--.

Claim 25, col. 14, line 56, after "claim 24", insert --,--.

Signed and Sealed this

Fourth Day of July, 2000

Q. TODD DICKINSON

*Attest:*

*Attesting Officer*   *Director of Patents and Trademarks*